United States Patent
Cohen et al.

(10) Patent No.: US 9,422,561 B2
(45) Date of Patent: Aug. 23, 2016

(54) TREATMENT OF DISEASE BY MODULATION OF SIRT6

(71) Applicant: BAR-ILAN UNIVERSITY, Ramat Gan (IL)

(72) Inventors: Haim Cohen, Modiin (IL); Yariv Kanfi, Petach Tikva (IL); Sivan Elhanati, Petach Tikva (IL)

(73) Assignee: BAR-ILAN UNIVERSITY, Ramat Gan (IL)

( * ) Notice: Subject to any disclaimer, the term of this patent is extended or adjusted under 35 U.S.C. 154(b) by 110 days.

(21) Appl. No.: 14/374,229

(22) PCT Filed: Jan. 24, 2013

(86) PCT No.: PCT/IB2013/050607
§ 371 (c)(1),
(2) Date: Jul. 24, 2014

(87) PCT Pub. No.: WO2013/111081
PCT Pub. Date: Aug. 1, 2013

(65) Prior Publication Data
US 2015/0018405 A1 Jan. 15, 2015

Related U.S. Application Data

(60) Provisional application No. 61/632,391, filed on Jan. 24, 2012.

(51) Int. Cl.
| | | |
|---|---|---|
| *C07H 21/02* | (2006.01) | |
| *C07H 21/04* | (2006.01) | |
| *A61K 31/70* | (2006.01) | |
| *C12N 15/113* | (2010.01) | |
| *A61K 31/713* | (2006.01) | |
| *C12N 9/80* | (2006.01) | |
| *C12N 5/00* | (2006.01) | |

(52) U.S. Cl.
CPC ......... *C12N 15/1137* (2013.01); *A61K 31/713* (2013.01); *C12N 9/80* (2013.01); *C12N 15/113* (2013.01); *C12N 2310/113* (2013.01); *C12N 2310/141* (2013.01); *C12Y 305/01* (2013.01)

(58) Field of Classification Search
None
See application file for complete search history.

(56) References Cited

U.S. PATENT DOCUMENTS

| 2011/0318284 A1 | 12/2011 | Dan Farra et al. | |
| 2013/0072421 A1* | 3/2013 | Collard | A61K 31/7088 514/1.6 |

FOREIGN PATENT DOCUMENTS

| WO | 2006078941 | 7/2006 |
| WO | 2008032048 | 2/2008 |
| WO | 2011011700 | 1/2011 |
| WO | 2011038110 | 3/2011 |
| WO | 2011081945 | 7/2011 |
| WO | 2011139387 A1 | 11/2011 |
| WO | 2012001245 | 1/2012 |
| WO | 2012027601 A2 | 3/2012 |

OTHER PUBLICATIONS

International Search Report mailed on Jun. 5, 2013 for PCT/IB2013/050607 filed on Jan. 24, 2013.
Esau, C., et al.; miR-122 regulation of lipid metabolism revealed by in vivo antisense targeting; Cell Metabolism Feb. 3, 2006, pp. 87-98; Retrieved from the Internet: <URL: http://www.cell.com/cell-metabolism/retrieve/pii/S15504131 06000295> Feb. 1, 2006.
Davalos, A. et al. miR-33a/b contribute to the regulation of fatty acid metabolism and insulin signaling. Proc Natl Acad Science USA; May 31, 2011; vol. 108 No. 22; pp. 9232-9237; Retrieved from the Internet: <URL: http://www.pnas.org/content/108/22/9232.long> May 16, 2011.
Rayner K.J. et al. MiR-33 contributes to the regulation of cholesterol homeostasis; Science. Jun. 18, 2010; 328(5985): 1570-1573. Retrieved from the Internet: <URL:http://www.ncbi.nlm.nih.gov/pmc/articles/PMC3114628/ > ; May 13, 2010.
Iliopoulos D., et al. MicroRNA-370 controls the expression of MicroRNA-122 and Cpt1 and affects lipid metabolism; J Lipid Res. Jun. 2010 ;51( 6): pp. 1513-1523 Retrieved from the Internet: <URL: http://www.jlr.org/cgi/pmidlookup?view=long&pmid=20 124555>; Feb. 2, 2010.
Mostoslaysky R., et al.; Genomic instability and aging-like phenotype in the absence of mammalian SIRT6. Cell 124; Jan. 27, 2006;124(2); pp. 315-329. Retrieved from the Internet: <URL:http://www.cell.com/retrieve/pii/S0092867406000493 >; Jan. 27, 2006.
Kanfi Y, et al. SIRT6 protects against pathological damage caused by diet-induced obesity; Aging Cell Apr. 2010, vol. 9(2); pp. 162-173. Retrieved from the Internet: <URL: http://onlinelibrary.wiley.com/doV 10.1111/j.474-9726.2009.00544.x/abstract;jsessionid=92EEB9EE8BF635DF8CBBD2AI40AIAA52. d02t02> Dec. 28, 2009.
Kim, D.H. and Rossi, J.J. Strategies for silencing human disease using RNA interference. Nature Reviews Genetics, Nature Publishing Group, vol. 8, Mar. 2007; pp. 173-184.

(Continued)

*Primary Examiner* — Sean McGarry
(74) *Attorney, Agent, or Firm* — A.C. Entis-IP Ltd.

(57) ABSTRACT

An aspect of an embodiment of the invention relates to providing treatment of disease, in particular age-related disease, through increasing or decreasing the activity of SIRT6 protein. This may be accomplished through upregulation and downregulation of expression of SIRT6 in mammals. It has been found by the inventors that mice overexpressing SIRT6 have a longer lifespan in comparison to control mice, indicating that increasing SIRT6 expression can lengthen lifespan of mammals. Agents which modulate SIRT6 expression through, for example binding to 3'UTR region of human mRNA encoding SIRT6 or by blocking binding of agents to 3'UTR region of human mRNA encoding SIRT6, have been identified.

22 Claims, 12 Drawing Sheets

(56) References Cited

OTHER PUBLICATIONS

Yuan et al; Aging in inbred strains of mice: study design and interim report on median lifespans and circulating IGF1levels; Aging Cell Jun. 2009; 8(3); pp. 277-287.

Wang, C. et al.; Statistical methods for testing effects on 'maximum lifespan'. Mechanisms of Ageing and Development 125, 2004; pp. 629-632.

Kasinski Andrea L and Slack Frank J. MicroRNAs en route to the clinic progress in validating and targeting microRNAs for cancer therapy; Dec. 2011; vol. 11; pp. 849-864.

* cited by examiner

SEQ ID NO. 1

```
GCTTCCGGCGGAAGCGGCCTCAACAAGGGAAACTTTATTGTTCCCGTGGGGCAGTCGAGGATGTCGGTGA
ATTACGCGGCGGGCTGTCCCGTACGCGGACAAGGGCAAGTGCGGCCTCCCGGAGATCTTCGACCCCCC
GGAGGAGCTGCAGCGGAAGCTGTGGGAACTGGCGAGGCTGGTCTGGCAGTCTTCCAGTGTGGTGTTCCAC
ACGGGTGCCGGCATCAGCACTGCCTCTGGCATCCCCCACTTCAGGGGTCCCCACGGAGTCTGGACCATGG
AGGAGCGAGGTCTGGCCCCCAAGTTCGACACCACCTTTGAGAGCGCGCGGCCCACGCAGACCCACATGGC
GCTGGTCCAGCTGGAGCGCGTGGGCCTCCTCCGCTTCCTGGTCAGCCAGAACGTGGACGGGCTCCATGTG
CGCTCAGGCTTCCCCAGGGACAAACTGGCAGAGCTCCACGGGAACATGTTTGTGGAAGAATGTGCCAAGT
GTAAGACGCAGTACGTCCGAGACACAGTCGTGGGCACCATGGGCCTGAAGGCCACGGCCGGCTCTGCAC
CGTGGCTAAGGCAAGGGGCTGCGAGCCTGCAGGGGAGAGCTGAGGGACACCATCCTAGACTGGGAGGAC
TCCCTGCCCGACCGGGACCTGGCACTCGCCGATGAGGCCAGCAGGAACGCCGACCTGTCCATCACGCTGG
GTACATCGCTGCAGATCCGGCCCAGCGGGAACCTGCCGCTGGCTACCAAGCGCCGGGCACGCCGCCTGGT
CATCGTCAACCTGCAGCCCACCAAGCACGACGGCCATCCTGACCTCCGCATCCATGGCTACGTTGACGAG
GTCATGACCCGGCTCATGAAGCACCTGGGGCTGGAGATCCCCGCCTGGGACGGCCCCCGTGTGCTGGAGA
GGGCGCTGCCACCCCTGCCCGGCCTGCCCACCCCAAGCTGGAGCCCAAGGAGGAATCTCCCACCCGGAT
CAACGGCTCTATCCCCGCCGGCCCCAAGCAGGAGCCCTGCGCCCAGCACAACGGCTCAGAGCCCGCCAGC
CCCAAACGGCAGCCGGCCCACCAGCCCTGCCCCCACAGACCCCCCAAAAGGGTGAAGGCCAAGGCGGTCC
CCAGCTGACCAGGGTGCTTGGGGAGGGTGGGGCTTTTGTAGAAACTGTGGATTCTTTTTCTCTCGTGGT
CTCACTTTGTTACTTGTTTCTGTCCCCGGGAGCCTCAGGGCTCTGAGAGCTGTGCTCCAGGCCAGGGCTT
ACACCTGCCCTCCGTGGTCCCTCCCTGGGCTCCAGGGGCCTCTGGTGCCGTTCCGGGAAGAAGCCACACC
CCAGAGGTGACAGGTGAGCCCCTGCCACACCCCAGCCTCTGACTTGCTGTGTTGTCCAGAGGTGAGGCTG
GGCCCTCCCTGGTCTCCAGCTTAAACAGGAGTGAACTCCCTCTGTCCCCAGGGCCTCCCTTCTGGCCCC
CTACAGCCCACCCTACCCCTCCTCCATGGGCCCTGCACGAGGGAGACCCACCTTGAAGTGGGGATCAG
TAGAGGCTTGCACTGCCTTTGGGGCTGGAGGGAGACGTGGGTCCACCAGGCTTCTGGAAAAGTCCTCAAT
GCAATAAAAACAATTTCTTTCTTGCAAAAAAAAAAAAAAAAAAAA
```

Fig. 2

SEQ. ID NO. 2

CCAGGGUGCUUGGGGAGGGUGGGGCUUUUUGUAGAAACUGUGGAUUCUUUUUCUCUCGUGGUCUCAC
UUUGUUACUUGUUUCUGUCCCCGGGAGCCUCAGGGCUCUGAGAGCUGUGCUCCAGGCCAGGGGUUACA
CCUGCCCUCCGUGGUCCCUCCCUGGGCUCCAGGGGCCUCUGGUGCGGUUCCGGGAAGAAGCCA<u>CACCCC</u>
<u>AG</u>AGGUGACAGCUGAGCCCCUGCCACACCCCAGCCUCUGACUUGCUGUGUUGUCCAGAGGUGAGGCUGG
GCCCUCCCUGGUCUCCAGCUUAAACAGGAGUGAACUCCCUCUGUCCCCAGGGCCUCCCUUCUGGGCCCCC
UACAGC<u>CCACCCUACC</u>CCUCCUCCAUGGGCCCUGCAGGAGGGG<u>AGACCCACCU</u>UGAAGUGGGGGAUCAG
UAGAGGCUUGCACUGCCUUUGGGGCUGGAGGGAGACGUGGGU<u>CCACCAGGC</u>UUCUGGAAAAGUCCU<u>CA</u>
<u>AUGCAA</u>UAAAAACAAUUUCUUUCUUGCAAA

Fig. 3

SEQ. ID NO. 3

GUGCAUUGUAGUUGCAUUGCA

SEQ. ID NO. 4

GUGCAUUGCUGUUGCAUUGC

SEQ. ID NO. 5

UGGAGUGUGACAAUGGUGUUUG

SEQ. ID NO. 6

GCCUGCUGGGGUGGAACCUGGU

Fig. 4

| SIRT 6 3'UTR nucleotides and miR alignment | Sequence |
|---|---|
| 479-486 | 5' ...UUCUGGAAAAGUCCUCAAUGCAA... |
| miR-33a | 3'     ACGUUACGUUGAUGUUACGUG |
| 479-486 | 5' ...UUCUGGAAAAGUCCUCAAUGCAA... |
| miR-33b | 3'     CGUUACGUUGUCGUUACGUG |
| 386-394 | 5'              ...AGAC CCACCU |
| miR-122 | 3' GUUUGUGGUAACAGUGUGAGGU |

Fig. 5

SEQ. ID NO. 7

UGCAAUGCAACUACAAUGCAC

SEQ. ID NO. 8

GCAAUGCAACAGCAAUGCAC

SEQ. ID NO. 9

CAAACACCAUUGUCACACUCCA

SEQ. ID NO. 10

GCCUGCUGGGGUGGAACCUGGU

Fig. 6

AntimiR-122 over-expression

SEQUENCE LISTING

<160> NUMBER OF SEQ ID NOS: 10

<210> SEQ ID NO 1
<211> LENGTH: 1657
<212> TYPE: DNA
<213> ORGANISM: Homo sapiens

<400> SEQUENCE: 1

```
gcttccggcg gaagcggcct caacaaggga aactttattg ttcccgtggg gcagtcgagg      60
atgtcggtga attacgcggc ggggctgtcg ccgtacgcgg acaagggcaa gtgcggcctc     120
ccggagatct tcgaccccc ggaggagctg gagcggaagg tgtgggaact ggcgaggctg     180
gtctggcagt cttccagtgt ggtgttccac acgggtgccg gcatcagcac tgcctctggc     240
atccccgact tcagggtcc ccacggagtc tggaccatgg aggagcgagg tctggccccc     300
aagttcgaca ccacctttga gagcgcgcgg cccacgcaga cccacatggc gctggtgcag     360
ctggagcgcg tgggcctcct ccgcttcctg gtcagccaga acgtggacgg gctccatgtg     420
cgctcaggct tccccaggga caaactggca gagctccacg ggaacatgtt tgtggaagaa     480
tgtgccaagt gtaagacgca gtacgtccga gacacagtcg tgggcaccat gggcctgaag     540
gccacgggcc ggctctgcac cgtggctaag gcaaggggc tgcgagcctg caggggagag     600
ctgagggaca ccatcctaga ctgggaggac tccctgcccg accgggacct ggcactcgcc     660
gatgaggcca gcaggaacgc cgacctgtcc atcacgctgg gtacatcgct gcagatccgg     720
cccagcggga acctgccgct ggctaccaag cgccggggag gccgcctggt catcgtcaac     780
ctgcagccca ccaagcacga ccgccatgct gacctccgca tccatggcta cgttgacgag     840
gtcatgaccc ggctcatgaa gcacctgggg ctggagatcc ccgcctggga cggccccgt     900 gtgctggaga gggcgctgcc accctgccc cgcccgccca ccccaagct ggagcccaag     960 gaggaatctc ccacccggat caacggctct atccccgccg gccccaagca ggagccctgc    1020
gcccagcaca acggctcaga gcccgccagc cccaaacggg agcggcccac cagccctgcc    1080
```

-continued

| | |
|---|---|
| ccccacagac ccccccaaaag ggtgaaggcc aaggcggtcc ccagctgacc agggtgcttg | 1140 |
| gggagggtgg ggcttttgt agaaactgtg gattctttt ctctcgtggt ctcactttgt | 1200 |
| tacttgtttc tgtccccggg agcctcaggg ctctgagagc tgtgctccag gccaggggtt | 1260 |
| acacctgccc tccgtggtcc ctccctgggc tccaggggcc tctggtgcgg ttccgggaag | 1320 |
| aagccacacc ccagaggtga caggtgagcc cctgccacac cccagcctct gacttgctgt | 1380 |
| gttgtccaga ggtgaggctg ggccctccct ggtctccagc ttaaacagga gtgaactccc | 1440 |
| tctgtcccca gggcctccct tctgggcccc ctacagccca ccctacccct cctccatggg | 1500 |
| ccctgcagga ggggagaccc accttgaagt gggggatcag tagaggcttg cactgccttt | 1560 |
| ggggctggag ggagacgtgg gtccaccagg cttctggaaa agtcctcaat gcaataaaaa | 1620 |
| caatttcttt cttgcaaaaa aaaaaaaaaa aaaaaa | 1657 |

<210> SEQ ID NO 2
<211> LENGTH: 510
<212> TYPE: RNA
<213> ORGANISM: Homo sapiens

<400> SEQUENCE: 2

| | |
|---|---|
| ccagggugcu uggggagggu ggggcuuuuu guagaaacug uggauucuuu uucucucgug | 60 |
| gucucacuuu guuacuuguu ucugucccccg ggagccucag ggcucugaga gcugugcucc | 120 |
| aggccagggg uuacaccugc ccuccguggu cccucccugg gcuccagggg ccucuggugc | 180 |
| gguuccggga agaagccaca ccccagaggu gacagcugag ccccugccac acccagccu | 240 |
| cugacuugcu guguugucca gaggugaggc ugggcccucc cuggucucca gcuuaaacag | 300 |
| gagugaacuc ccucugucccc cagggccucc cuucugggcc cccuacagcc cacccuaccc | 360 |
| cuccuccaug ggcccugcag gagggagac ccaccuugaa gugggggauc aguagaggcu | 420 |
| ugcacugccu uuggggcugg agggagacgu gguccaccag gcuucuggaa aaguccuca | 480 |
| augcaauaaa aacaauuucu uucuugcaaa | 510 |

<210> SEQ ID NO 3
<211> LENGTH: 21
<212> TYPE: RNA
<213> ORGANISM: Homo sapiens

<400> SEQUENCE: 3

| | |
|---|---|
| gugcauugua guugcauugc a | 21 |

<210> SEQ ID NO 4
<211> LENGTH: 20
<212> TYPE: RNA
<213> ORGANISM: Homo sapiens

<400> SEQUENCE: 4

| | |
|---|---|
| gugcauugcu guugcauugc | 20 |

<210> SEQ ID NO 5
<211> LENGTH: 22
<212> TYPE: RNA
<213> ORGANISM: Homo sapiens

<400> SEQUENCE: 5

| | |
|---|---|
| uggaguguga caauggucguu ug | 22 |

<210> SEQ ID NO 6
<211> LENGTH: 22

```
<212> TYPE: RNA
<213> ORGANISM: Homo sapiens

<400> SEQUENCE: 6
gccugcuggg guggaaccug gu                                                22

<210> SEQ ID NO 7
<211> LENGTH: 21
<212> TYPE: RNA
<213> ORGANISM: Artificial Sequence
<220> FEATURE:
<223> OTHER INFORMATION: anti-miR-33a

<400> SEQUENCE: 7
ugcaaugcaa cuacaaugca c                                                 21

<210> SEQ ID NO 8
<211> LENGTH: 20
<212> TYPE: RNA
<213> ORGANISM: Artificial Sequence
<220> FEATURE:
<223> OTHER INFORMATION: anti-miR-33b

<400> SEQUENCE: 8
gcaaugcaac agcaaugcac                                                   20

<210> SEQ ID NO 9
<211> LENGTH: 22
<212> TYPE: RNA
<213> ORGANISM: Artificial Sequence
<220> FEATURE:
<223> OTHER INFORMATION: anti-miR-122

<400> SEQUENCE: 9
caaacaccau ugucacacuc ca                                                22

<210> SEQ ID NO 10
<211> LENGTH: 22
<212> TYPE: RNA
<213> ORGANISM: Artificial Sequence
<220> FEATURE:
<223> OTHER INFORMATION: antimiR-370

<400> SEQUENCE: 10
gccugcuggg guggaaccug gu                                                22
```

TREATMENT OF DISEASE BY MODULATION OF SIRT6

RELATED APPLICATIONS

The present application is a US National Phase of PCT Application No. PCT/IB2013/050607, filed on Jan. 24, 2013, which claims the benefit under 35 U.S.C. 119(e) of U.S. Provisional Application 61/632,391 filed on Jan. 24, 2012, the disclosure of which are incorporated herein by reference.

TECHNICAL FIELD

Embodiments of the invention relate to treatment of diseases.

BACKGROUND

Sirtuin proteins (also known as Sir2 proteins and silent mating type information regulation 2 proteins) are a family of proteins that regulate biological pathways in various organisms including bacteria, yeasts and mammals. Yeast sirtuin has been well characterized, and homologs known as SIRT1 through SIRT7 have been identified in humans. These proteins may act as deacetylases, lysine malonyl transferases or ADP (adenosine diphosphate) ribosyl transferases and regulate various activities within cells.

The sirtuin-6 (SIRT6) protein, encoded by the SIRT6 gene, is a protein that has been associated with energy metabolism.

SUMMARY

An aspect of an embodiment of the invention relates to providing treatment of disease through increasing or decreasing the activity of SIRT6 protein. This may be accomplished through upregulation and downregulation of expression of SIRT6 in mammals. The effect of up-regulating and down-regulating SIRT6 expression was shown in animal models. Although some mammalian sirtuins were previously shown to regulate age-related diseases, mice overexpres sing SIRT1 retain the same lifespan as control wild type (WT) mice. It has been found by the inventors that mice over-expressing SIRT6 have a longer lifespan in comparison to control mice, indicating that increasing SIRT6 expression can lengthen lifespan of mammals.

According to an aspect of an embodiment of the invention therapeutic agents which increase the activity of SIRT6 or upregulate SIRT6 expression may be used to increase human lifespan and to control age related diseases. "Increasing activity of SIRT6" may refer to both increasing protein activity, quality or quantity in an organism and to upregulating expression of the SIRT6 gene, thereby producing SIRT6 protein to a greater extent.

An aspect of an embodiment of the invention relates to providing a method for treating an age-related disease comprising administering to a human patient in need thereof an agent which increases the expression of the SIRT6 gene.

An embodiment of the invention relates to providing a method for treating an age-related disease comprising administering to a human patient in need thereof an agent which activates SIRT6 protein in a human patient.

An embodiment of the invention relates to providing a method for treating cancer comprising administering to a human patient in need thereof an agent, to decrease the activity of SIRT6 in cancer cells. "Decreasing activity of SIRT6," may refer to both decreasing protein activity, quality or quantity in an organism and to downregulating expression of the SIRT6 gene, thereby producing SIRT6 protein to a lesser extent.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph.

FIG. 2 depicts a human DNA sequence (referred to as SEQ. ID NO. 1) corresponding to mRNA encoding SIRT6, including its three prime untranslated (3'UTR) region;

FIG. 3 depicts the 3'UTR region of human mRNA encoding SIRT6 (referred to as SEQ. ID NO. 2) with nucleotides 479-486 and nucleotides 386-394 underlined, and nucleotides 199-206, nucleotides 350-359 and nucleotides 455-463 double underlined;

FIG. 4 depicts miRNA sequences of miR-33a, miR-33b, miR-122, miR-370 referred to as SEQ. ID NO. 3, SEQ. ID NO. 4, SEQ. ID NO. 5 and SEQ. ID NO. 6 respectively, agents which may be used to downregulate SIRT6 expression in accordance with an embodiment of the invention;

FIG. 5 depicts miRNA sequences of miR-33a, miR-33b and miR-122, referred to as SEQ. ID NO. 3, SEQ. ID NO. 4 and SEQ. ID NO. 5, respectively bound to their corresponding binding sites on 3' UTR SIRT6 mRNA;

FIG. 6 depicts sequences of antimiR-33a, antimiR-33b and antimiR-122, referred to as SEQ. ID NO. 7, SEQ. ID NO. 8, SEQ. ID NO. 9 and SEQ. ID NO. 10, respectively, agents which may be used to upregulate SIRT6 expression in accordance with an embodiment of the invention;

Figure 8A:
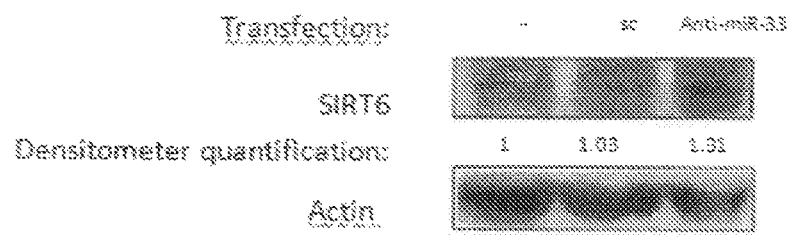
Figure 8B:
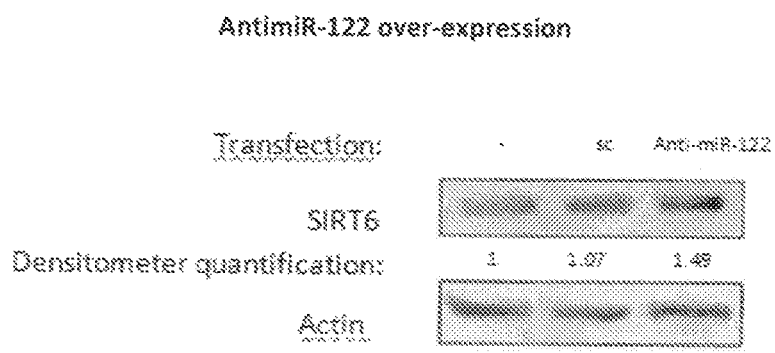
Figure 9:
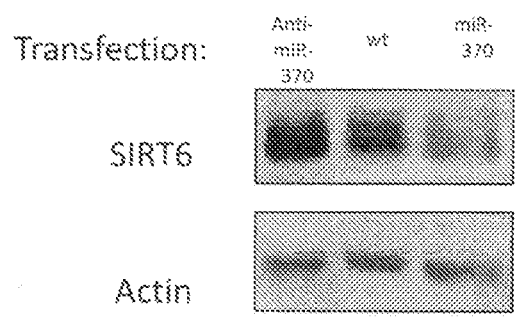

7B), as indicated using western blot analysis by lighter band in miR-transfected cells as compared to control (indicated by "−") and vehicle cells;

FIGS. 8A-B show upregulation of SIRT6 expression in cells transfected by antimiR-33a (FIG. 8A) and antimiR-122 (FIG. 8B) as indicated by western blot analysis by heavier band in antimiR-transfected cells as compared to control and scramble sequence (sc) transfected cells;

FIG. 9 shows upregulation SIRT6 expression in cells transfected by antimiR-370 and downregulation of SIRT6 expression in cells tranfected by miR-370 as indicated by western blot analysis by a heavier band in antimiR-transfected cells as compared to WT cells and by a lighter band in miR tranfected cells, as compared to WT cells.

DETAILED DESCRIPTION

The examples detailed in the following paragraphs illustrate the therapeutic effect of upregulation or downregulation of SIRT6. In particular, example 1 illustrates that SIRT6 upregulation in mammals prolongs lifespan and may prevent age related disease. Example 2 describes agents that have been identified to upregulate and downregulate SIRT6 expression and may be used, according to embodiments of the invention, for treatment of age-related disease.

Example 1A

Increased Lifespan of Transgenic Mice Over-Expressing SIRT6

In this example, lifespan of Sirt6-tg mice was examined in comparison to their control littermates. Sirt6-tg mice were produced using CB6F1 strain, and maintained on a segregating stock containing equal contributions of C57BL/6J and BALB/cOlaHsd (Harlan laboratories) backgrounds, both considered to be long lived strains, as previously described (Yuan 2009). The experiment was performed on 245 mice (119 males and 126 females) from two transgenic lines generated from two separate founders.

In a period of about three months, each male founder (heterozygous for the transgene) was bred with WT CB6F1 females and the progeny were used for the life-span analysis. The integration site in each line of the transgene was mapped by nested inverse polymerase chain reaction ("PCR"), with several different restriction enzymes from both the right and left of the integration site and found to be in noncoding regions. Results were validated with sequencing and additional PCR confirming integration sites. Mice were kept under specific pathogen free conditions in individually ventilated cages, "IVC cages" that were routinely examined and found negative for viral serology and both endo and ectoparasites. The mice were raised under 12 h day/night conditions and had free access to standard chow diet and water. All mice were left undisturbed until natural death. Mice tested at all ages were not part of the life-span cohort.

Figures 1A, 1B:
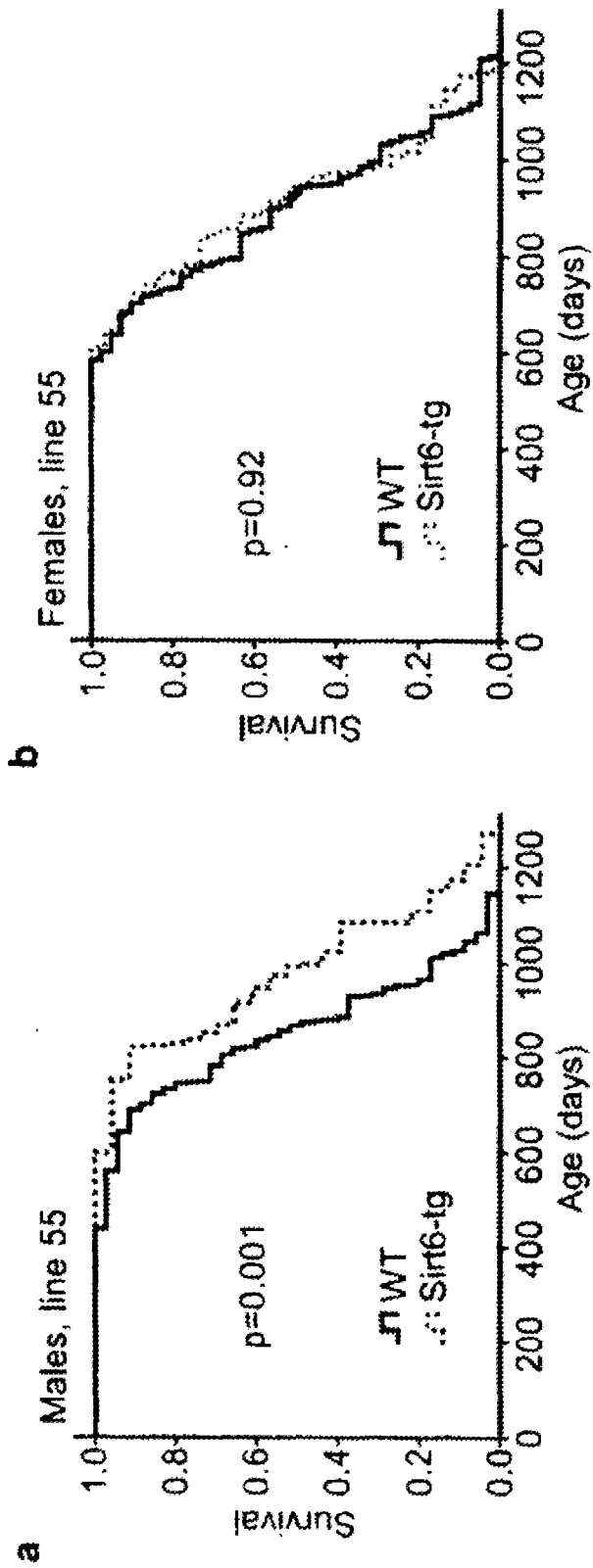
FIGS. 1a and 1b depict survival curves showing percent survival over time for transgenic SIRT-6 overexpressing (SIRT6-tg) male (FIG. 1a) and female (FIG. 1b) mice from a strain designated as line 55 and WT control mice.
Figures 1C, 1D:
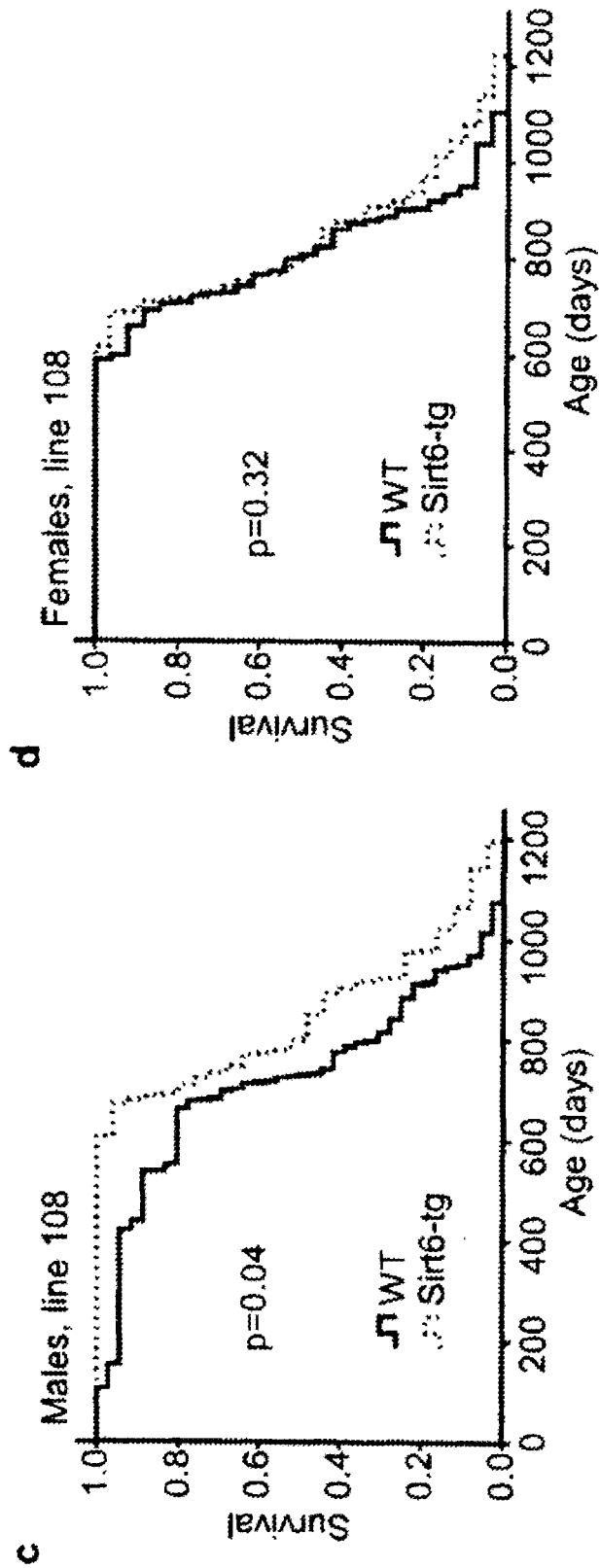
FIGS. 1c and 1d depict survival curves showing percent survival over time for SIRT6-tg male (FIG. 1c) and female (FIG. 1d) mice from a strain designated as line 108 and WT control mice.

Log-rank test analysis showed significant differences in the survival curves between WT and transgenic male mice lines 55 and 108 (FIGS. 1a and 1c respectively) but not between WT and transgenic female mice in both lines (FIGS. 1b and 1d.) In male Sirt6-tg mice median lifespan increased by 14.5% and 9.9% and mean lifespan increased by 14.8% and 16.9% relative to male WT littermates, lines 55 and 108 respectively. In female Sirt6-tg mice no significant increase in median or mean lifespan was found relative to female WT littermates in both lines. Males' maximum lifespan (mean lifespan of oldest 10% within a cohort to die) increased by 15.8% and 13.1% relative to that of WT littermates mice, lines 55 and 108 respectively. In summary, SIRT6 overexpression increased longevity in males but not in females.

SIRT6 was shown to regulate genome stability and metabolism, two major contributors to longevity. Loss of genomic stability is known to be an important aspect of cancer. Postmortem gross and microscopic examination of mice revealed malignant tumors in a variety of organs, although the highest incidence of tumors in all mice was found to be in the lungs. A comparison of median lifespan between WT and Sirt6-tg mice with lung tumors shows a trend of increased lifespan in transgenic mice of 11.7%. Therefore, it is suggested that SIRT6 has an effect on cancer, in particular, in lung cancer which plays a role in SIRT6's pro-longevity effect.

SIRT6 might positively affect age-associated metabolic disorders such as declining insulin sensitivity and impaired glucose tolerance. Glucose metabolism was tested using the glucose tolerance test (GTT.) Mice were deprived of food overnight prior to GTT. 2 g (gram) of glucose per kg (kilogram) of body weight was injected via intraperitoneal injection. Blood glucose was measured on samples obtained by tail bleeding prior to glucose administration and after 15, 30, 60, 90, and 120 min (minutes) using glucometer test strips (Abbott).

Figures 1E, 1F:
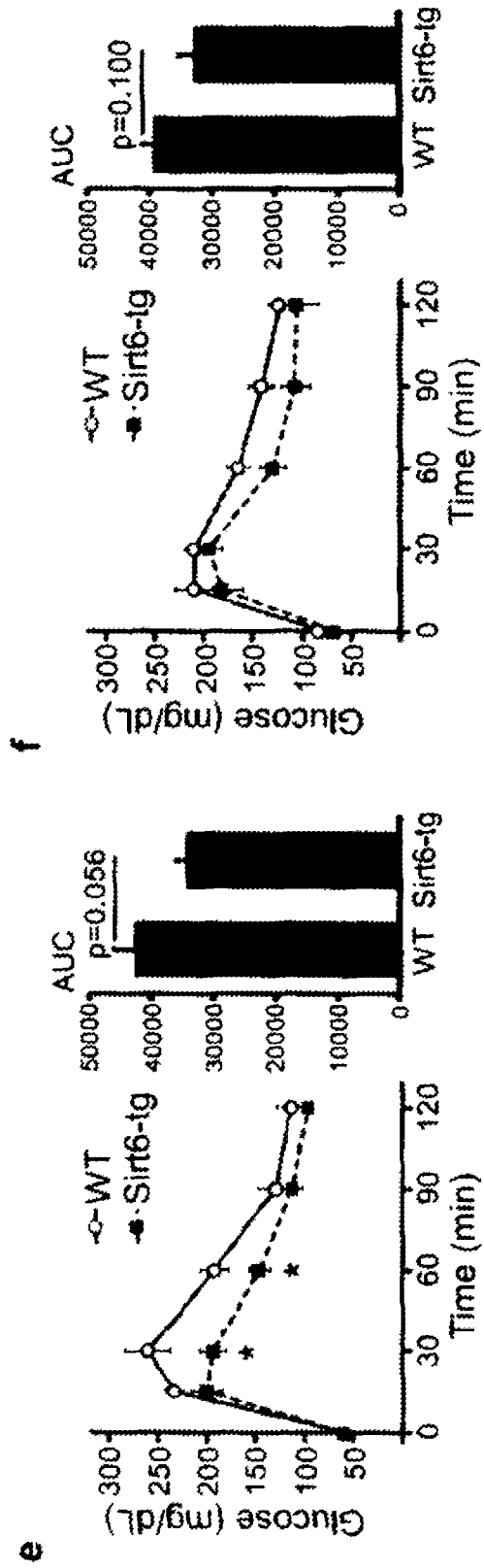
FIGS. 1e and 1f depict graphs showing results of a glucose tolerance test in SIRT6-tg male (FIG. 1e) and female (FIG. 1f) mice and WT control mice (old mice, aged 19 months) alongside bar graphs depicting area under curve (AUC) for each group.

No significant differences in glucose metabolism were found in young mice (4-7 months old). However, GTT showed that aged SIRT6-tg mice (19 months old, the maximal age of WT mice before appearance of major death) display a trend towards improved glucose homeostasis as evident in FIG. 1e (males, 6 mice per genotype) and 1f (females, 4 mice per genotype). Area under curve (AUC) for each GTT is shown on right. Values are expressed as mean±SEM. Asterisk signifies $P<0.05$, two-tailed t-test.

Statistical analyses were performed in SPSS (Version 17, SPSS Inc.) software using unpaired t tests, ANOVA, log rank and Cox regression analysis. Quantile regression was performed in order to analyze maximum life-span according to Wang et al. 2004, and P values were calculated using Fisher's exact test. Each line and gender were analyzed for life-span parameters separately. Results were expressed as mean±SEM. $P<0.05$ was regarded as statistically significant.

Example 1B

Decreased Body Fat of 2 Year Old Mice in Transgenic Mice Over-Expressing SIRT6

Transgenic mice were prepared as in example 1A. Body weight was determined in male and female transgenic and wild type mice at two years of age. In addition, percentage of body fat was determined using NMR technology.

Figure 1G:
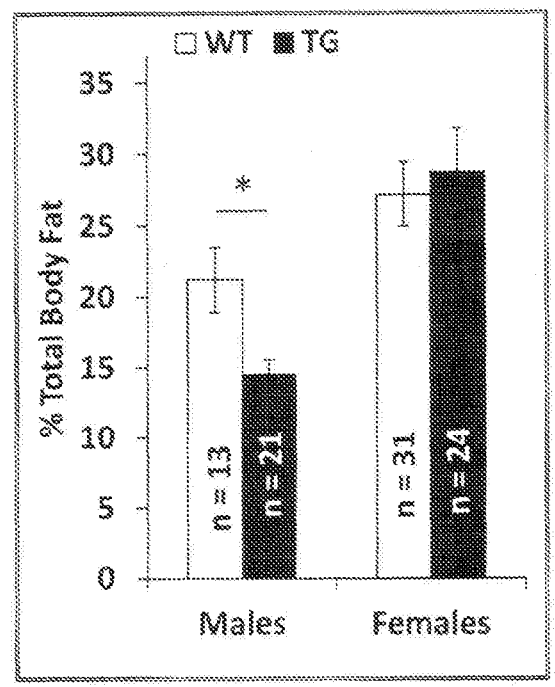
FIG. 1g depicts a graph showing percentage body fat in mice aged two years from SIRT6-tg and WT control mice groups.
Figure 1H:
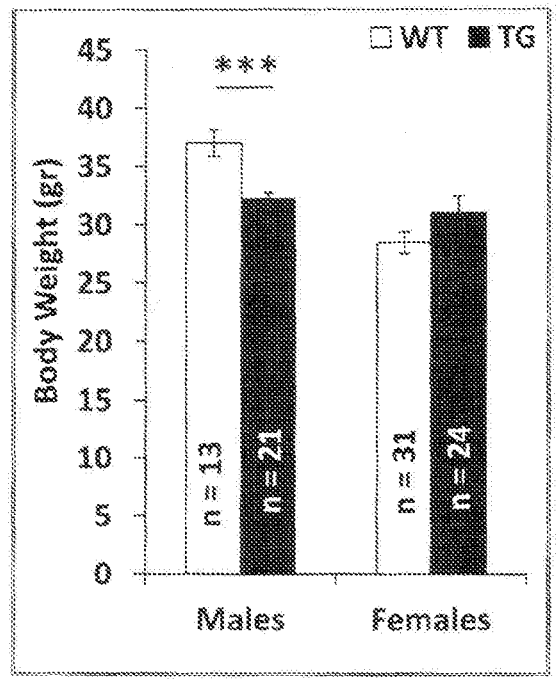
FIG. 1h depicts a graph showing body weight, in grams in mice aged two years from SIRT6-tg and WT control mice groups.

As shown in FIG. 1G, percentage of body fat for transgenic males was significantly lower than percentage of body fat for wild type males. As shown in FIG. 1H, weight was significantly lower for transgenic males than for wild type males. No significant differences in these two measures were found between wild type and transgenic females.

These results indicate that upregulation of SIRT6 may prevent age-induced obesity and diseases associated with age-induced obesity. Although the diets of both transgenic and wildtype groups were identical, and were not high-fat diets, the transgenic overexpressing mice showed less age-related weight gain and less age-related increased body fat content.

Example 2

RNA Interference

In mammalian cells, genetic material is stored in DNA in the cells' nuclei. In order to convert a cell's DNA into a protein or enzyme, transcription occurs in the cell nucleus, in which the DNA is used as a template which is "copied" to messenger RNA (mRNA) which is then transported out of the nucleus of the cell to be translated into a protein or enzyme at a ribosome, in the cell's cytoplasm. In the translation process, a ribosome builds a protein or enzyme based on the sequence of the mRNA.

The translation process is moderated in cells in many organisms in a process called RNA interference (RNAi.) In RNAi, small pieces of RNA called microRNA (miRNA) or small interfering RNA (siRNA) specifically block the translation of genes into proteins. RNAi technology can be used by introducing synthetic siRNA or miRNA into cells, thereby blocking expression of specific genes.

MiRNA is a short strand of RNA (about 20 nucleotides) which binds to a portion of mRNA and prevents the mRNA translation, thereby effectively "silencing" a gene. Generally, miRNA binds to a non-coding region of the mRNA, the three prime untranslated (3'UTR) region, but may also bind other regions. There are about 1000 naturally occurring miRNA sequences that have been identified to date.

The inventors have determined that the sequences of 4 human miRNAs are complementary to portions of the 3'UTR region of human SIRT6 mRNA. The 4 miRNAs which have been identified are miR-33a, miR-33b, miR-122 and miR-370. Their respective sequences SEQ. ID NO. 3, SEQ. ID NO. 4, SEQ. ID NO. 5 and SEQ. ID NO. 6 are depicted in FIG. 4, and binding sites of SEQ. ID NO. 3-5 on 3'UTR SIRT6 mRNA are shown in FIGS. 3 and 5. In FIG. 3, the binding sites of miR-122 and miR-33 are underlined, and the presumed binding sites of miR-370, nucleotides 199-206, nucleotides 350-359 and nucleotides 455-463, are double-underlined. The bold characters in FIG. 5 represent the presumed nucleotides of the miRNA involved in binding.

MiR-33a, miR-33b, miR-122 and miR-370 were cloned according to the following procedure. The human hepatoma cell line, known as HepG2, was used and grown in full DMEM medium supplemented with 10% fetal calf serum, penicillin-streptomycin mixture 100 units/ml and L-glutamine 100 units/ml (units/milliliters). For transfection, cells were grown to 50% confluence in a 6-well cell culture plate. After 24 hours, transfection was performed using the transfection reagent lipofectamine (Invitrogen.) The genomic DNA that encompass the miR in addition to 200 base pairs upstream and downstream was cloned and insterted into a vector called Mirvec. The following amounts of DNA were transfected: SIRT6: 2 µg (microgram) in a 6-well format. The total amount of DNA in each transfection was normalized with apcDNA3.1+vector. The cells were harvested 48 hours post transfection.

48 hours after transfection, western blot was performed using the following procedure: HepG2 cells were detached by scraping and then resuspended in lysis buffer [50 mM 4-(2-hydroxyethyl)-1-piperazineethanesulfonic acid (HEPES) (pH 7.5), 150 mM NaCl, 10% glycerol, 1% Triton X-100, 1 mM ethylenediaminetetraacetic acid, 1 mM ethylene glycol tetraacetic acid, and a protease inhibitor cocktail (diluted at 1:1000)], and incubated on ice for 15 min. Lysates were cleared by centrifugation (13,000 rpm, 15 minutes). For direct electrophoretic analysis, sample buffer (6x) was added to cell lysates, that were subsequently resolved by SDS-polyacrylamide gel and electrophoretically transferred to a nitrocellulose membrane. Membranes were blocked in Tris-Buffered Saline and Tween 20 (TBST) buffer [0.02M Tris-HCl (pH 7.5), 0.15M NaCl, and 0.05% Tween 20] containing 5% BSA, blotted with a primary antibody for 1 hour or overnight, washed in TBST, and incubated for 30 min with a secondary antibody linked to horseradish peroxidase. Immunoreactive bands were detected using enhanced chemiluminescence (ECL) reagents (Pierce, Rockford, Ill. USA).

Figure 7A:
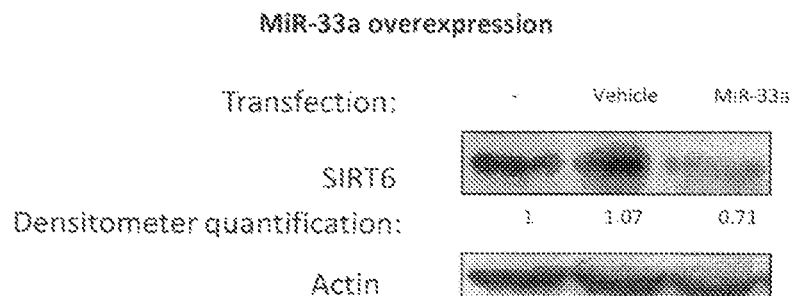
FIG. 7A-B show downregulation of SIRT6 expression in cells transfected by miR-33a (FIG. 7A), and miR-122 (FIG.
Figure 7B:
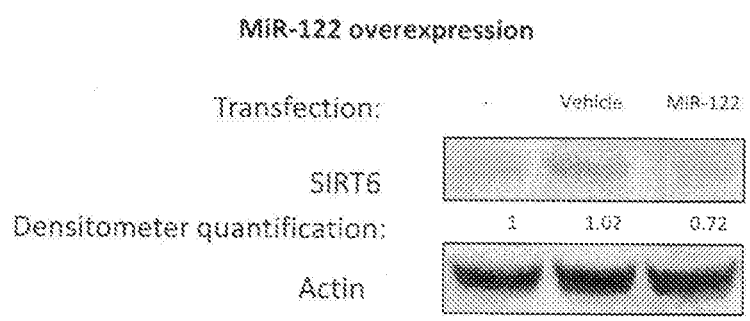

FIG. 7 shows results of a western blot analysis of SIRT6 expression in miR transfected cells as compared to control, untreated cells (−) and a vehicle vector. The actin bands serve as a loading control. Densitometer quantification of SIRT6 was performed for each band and was expressed relative to control, non-treated cells. These results show that transfection of miR-33a and miR-122 decreased the expression of SIRT6 in transfected cells.

An antimiR (also known as an antagomir) is a small synthetic RNA that is complementary to a specific miRNA target, and inhibit miRNA. AntimiR technology has been successfully used to inhibit fibrosis of heart and lung. AntimiR-33a, antimiR-33b, antimiR-122 and antimiR-370 (complementary to miR-33a, miR-33b, miR-122 and miR-370 respectively) were obtained from Applied Biosystems. The sequences are shown in SEQ. ID NO. 7, SEQ. ID NO. 8, SEQ. ID NO. 9 and SEQ. ID NO. 10 respectively, in FIG. 6.

The miRNA was transfected into HepG2 cells via reverse transfection. Cells were seeded in a 6-well plate. 24 hours after seeding they were transfected with antimiR-33a, antimiR-33b, antimiR-122 or antimiR-370 (final concentration: 30 nM).

In order to prepare the transfection medium, in a first tube, 100 µl (microliter) of serum-free medium was added to 5 µl siPORT NeoFX, a lipid based transfection agent available from Applied Biosystems, and the tube was mixed gently. In a second tube, 100 µl of serum-free medium was added to 7.5 µl antimiR (10 µM) and was mixed gently. After 10 min, the first and second tubes were mixed gently, and then after 10 min, the mixture was dispensed into an empty well, and 500,000 cells were seeded in each well to a final well volume of 2.5 ml. The wells were tilted back and forth. The cells were harvested 40-48 hours post transfection for further analysis in western blot.

Western blot was performed as described above. FIG. 8 shows results of SIRT6 expression using a western blot analysis of anti-miR transfected cells as compared to control, untreated cells (−) and cells transfected with a scramble sequence (sc). The actin bands serve as a loading control. Densitometer quantification of SIRT6 was performed for each band and was expressed relative to control, non-treated cells. Transfection of antimiR-33a and antimiR-122 increased the expression of SIRT6 in transfected cells.

FIG. 9 shows results of SIRT6 expression using a western blot analysis of antimiR-370 and miR-370 transfected cells as compared to control, untreated cells (wt). The actin bands serve as a loading control. These results show that transfection of miR-370 decreased the expression of SIRT6 in transfected cells, and transfection of anti-miR-370 increased the expression of SIRT6 in transfected cells.

AntimiR-33a, AntimiR-33b, AntimiR-122 and AntimiR-370 may each be agents useful for increasing expression of SIRT6 when administered to patients in need thereof.

Example 3

Identification of Agents Capable of Modulating SIRT6 Activity

In addition to the methods described above, a fluorometric assay was performed to identify agents capable of modulating SIRT6, including agents capable of activating SIRT6 using the following method.

The assay employs a short acetylated peptide based on amino acids 5-9 of histone H3K9 comprising an acetylated lysine residue, and labeled with a fluorophore, 7-amino-4-methylcoumarin (AMC) conjugated to the C-terminal end of the peptide. The AMC fluorophore emits fluorescence when free, but does not emit significant fluorescence in the conjugated state.

The procedure comprises two steps, both performed in the same microplate. In the first step, the substrate is incubated with human recombinant SIRT6 protein along with the co-enzyme Nicotinamide adenine dinucleotide (NAD+). SIRT6 will act to deacetylate the peptide. Upon deacetylation, the liberated ε-amino group of the lysine becomes a trypsin substrate. Treatment with trypsin in the second step releases the fluorophore resulting in an increase in fluorescence (excitation and emission at 350-360 nm and 450-465 nm, respectively). In the first step, SIRT6 can be incubated with agents capable of increasing or decreasing SIRT6 deacetylation activity. Increase in SIRT6 deacetylation may be detected by increased fluorescence relative to control microplates in which no modulating agent is added, and decrease in SIRT6 deacetylation may be detected by decreased fluorescence relative to control microplates.

Agents identified by this method which increase SIRT6 activity may be effective in treating age-related disorders in humans. Agents identified by this method which decrease SIRT6 activity may be effective in treating cancer in humans.

Example 4

Treatment of Mammals, Including Humans, Using Agents that Modulate SIRT6 Expression As shown in examples 1A and 1B, upregulation of SIRT6 expression in mammals may increase life span and reduce age-related obesity. In addition, upregulation of SIRT6 expression in mammals has shown effect in diseases relating to glucose metabolism and cancer. Accordingly, an aspect of an embodiment of the invention relates to providing a method for treating an age-related disease comprising administering to a human patient in need thereof an agent which increases the expression of the SIRT6 gene.

As shown in example 2, agents were found which can bind to the mRNA sequence of SIRT6 (SEQ. ID NO. 2) and down-regulate its expression (decrease SIRT6 expression) and therefore may be used to treat disease. In addition, it has been found that there are agents which upregulate expression of SIRT6 (increase SIRT6 expression) by interfering with naturally occurring agents that downregulate SIRT6 expression, and therefore may be used to treat disease, in particular age-related disease.

In an embodiment of the invention, the age-related disease is selected from the group consisting of neurodegenerative disease, cancer, cardiovascular disease, obesity, type 2 diabetes, increased cholesterol levels, hypertension, ocular disorders including cataracts and glaucoma, osteoporosis, blood clotting disorders, arthritis, hearing loss, stroke and Alzheimer's disease. In an embodiment, the age-related disease is treated in a patient above the age of 50. In an embodiment, the age-related disease is treated in a patient above the age of 65. In an embodiment, the age-related disease is treated in a patient above the age of 80.

In an embdodiment of the invention, the neurodegenerative disease is associated with degeneration of neural tissue. In an embdodiment of the invention, the neurodegenerative disease is selected from the group consisting of: Alzheimer's disease, Parkinson's disease, Huntington's diseases, amyotrophic lateral sclerosis and multiple system atrophy.

In an embodiment of the invention, cardiovascular disease is a disease afflicting the heart and/or blood vessels. In an embodiment of the invention, cardiovascular disease is selected from the group consisting of: coronary heart diseases, cardiomyopathy, hypertensive heart diseases, cardiac dysrhythmias, endocarditis, cardiomegaly, myocarditis, calcular heart diseases, cerebrovascular disease and peripheral arterial disease.

In the treatment of age related diseases, agents that increase the activity of SIRT6 may be administered systemically, for example intravenously. In an embodiment of the invention, an agent capable of modulating activity of SIRT6, hereinafter, "active agent," is combined with at least one pharmaceutically acceptable excipient to form a pharmaceutical composition comprising an active agent. In an embodiment of the invention, the pharmaceutical composition is adapted for human or animal use via oral, rectal, vaginal, topical, nasal, ophthalmic, transdermal, subcutaneous, intramuscular, intraperitoneal or intravenous administration.

The pharmaceutical compositions according to an embodiment of the invention may be conveniently presented in unit dosage form and are prepared by any of the methods well known in the art of pharmacy. In an embodiment of the invention, the unit dosage form is in the form of a tablet, capsule, lozenge, wafer, patch, ampoule, vial or pre-filled syringe.

The pharmaceutical compositions according to the present invention are generally administered in the form of a pharmaceutical composition comprising at least one active component together with a pharmaceutically acceptable carrier or diluent.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the components of this invention can be combined with various sweetening agents, flavoring agents, coloring agents, emulsifying agents and/or suspending agents, as well as such diluents as water, ethanol, propylene glycol, glycerin and various like combinations thereof.

The compositions according to embodiments of this invention may also be administered in a controlled release formulation such as a slow release or a fast release formulation. Such controlled release dosage composition may be prepared using methods well known to those skilled in the art.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes.

Pharmaceutical compositions according to embodiments of the invention may contain an amount of 0.1%-95% of the active agent, preferably 1%-70%.

In an embodiment of the invention, the daily dosage of the active agent is between 0.001 mg and 3000 mg.

In an embodiment of the invention, the agent which upregulates the expression of the SIRT6 gene interferes with the activity of miRNA.

Various antimiRs have proven to be effective in mammalian administration in upregulation of gene expression. AntimiRs have been used in treatment of hepatitis C virus-infected non-human primates. In an embodiment of the invention, the agent is anti-miRNA. In an embodiment, the anti-miRNA is antimiR-33a, antimiR-33b, antimiR-122 or antimiR-370, or a combination thereof.

Administration of antimiRs may be administered to a patient and will target specific cells in which there is a high presence of a specific miRNA. In an embodiment of the invention, miRNA or antimiR is administered to a patient and modulates SIRT6 expression in adipocytes or hepatocytes.

Downregulation of SIRT6 expression in mammalian cells may cause cell death in such cells. Downregulation of SIRT6 expression may be targeted to mammalian cancer cells, thereby causing cell death in those cells, thereby treating cancer in the mammal.

In the treatment of tumors, agents that downregulate expression of SIRT6 may be injected directly into tumors, thereby causing cell death within cancer cells.

In an embodiment of the invention, the agent which downregulates the expression of the SIRT6 gene is miRNA. In an embodiment, the miRNA has a region complementary to a region of SEQ. ID NO. 2 (in FIG. 3). In an embodiment, the miRNA has a region which is complementary to nucleotides 479-486 or nucleotides 386-394 of SEQ. ID NO. 2. In an embodiment, the miRNA is miR-33a, miR-33b or miR-122.

In addition to SIRT6 as depicted in SEQ. ID NO. 1 and SEQ. ID NO. 2 (FIGS. 2 and 3, respectively), other variants of human SIRT6 exist (including a shorter variant with 27 fewer amino acids,) and methods of upregulating and downregulating expression of variants of human SIRT6 are encompassed according to embodiments of the invention.

In addition to the miRNA and antimiR agents disclosed in example 2, siRNA is another type of RNAi which may be used to modulate expression of SIRT6 in mammalian cells by upregulating or downregulating expression, thereby treating the mammal.

RNA interfering agents can be delivered in a pharmaceutically acceptable carrier. One or more RNA interfering agents can be used simultaneously. A viral-mediated delivery mechanism can also be employed to deliver siRNAs to cells as described previously (Kim 2007).

There are a number of methods of delivery of siRNA, antimiR and miRNA to mammals in need of RNA interference. Non-selective approaches to delivery include linking cholesterol groups to chemically modified siRNAs for systemic delivery. In addition, siRNAs can be delivered systemically by stable nucleic acid-lipid particles (SNALPs). Alternatively, selective approaches can be used, including using Aptamer-siRNA chimaeras to allow siRNAs to be delivered to specific cell types that display receptors recognized by the aptamers. Heavy-chain antibody fragments (Fabs) and siRNAs can be linked with protamine to deliver siRNAs to specific cell-surface receptors. Nanoparticles that display specific ligands on their surfaces can be used to target siRNAs to particular cell types. Long-term RNAi may be mediated by viral expression vectors.

It is suggested according to embodiments of the present invention that cancer may be treated by upregulation of SIRT6 in an organism. This effect was evident in mice in example 1A. Without being bound by theory, it is suggested that upregulation of SIRT6 may have one or more of the following effects: 1. Increased levels of SIRT6 inhibit phosphorylation of c-Jun N-terminal kinase (JNK), leading to increased heat shock protein 72 (HSP72) levels, impacting obesity, neurodegenerative disorders, immune system function and cancer. 2. SIRT6 protects normal cells from DNA damage by stabilizing telomere matter. 3. Cancer cells are known to reproduce at a higher rate than normal cells based on the "Warburg effect" in which cancer cells rely on glycolysis for metabolism. SIRT6 expression is associated with an anti-glycolytic effect, thereby preventing cancer cells from increased metabolism and eliminating their ability to survive. 4. SIRT6 overexpression results in activation of AMP-activated protein kinase (AMPk) due to a significant increase in total AMPK, phosphorylated AMPK (Thr 172) and AMP/ATP ratio. Metformin, and thiazolidinedione-TZD, known AMPK activators, are to date the most subscribed medicine used for the treatment of type 2 diabetes. Thus, SIRT6 overexpression will impact diabetes and its associated disorders. In addition, AMPK is also known to inhibit the Warburg effect. Thus SIRT6 overexpression may block the aforementioned Warburg effect via activation of AMPK and may thereby limit cancer progression.

There is further provided, in accordance with an embodiment of the invention, a method for treating an age-related disease comprising administering to a human subject in need thereof an effective amount of an agent which increases the activity of sirtuin-6 (SIRT6). In an embodiment of the invention, the activity of SIRT6 is increased by administering to a human subject in need thereof an effective amount of an agent which increases the expression of the sirtuin-6 (SIRT6) gene. Optionally, the age-related disease is selected from the group consisting of: neurodegenerative disease, cancer, cardiovascular disease, obesity, type 2 diabetes, increased cholesterol levels, hypertension, ocular disorders including cataracts and glaucoma, osteoporosis, blood clotting disorders, arthritis, hearing loss, stroke and Alzheimer's disease. Optionally, the agent increases the expression of the SIRT6 gene by inhibiting binding of a SIRT6 expression inhibitor to a 3'UTR region of human mRNA encoding SIRT6. Optionally, the SIRT6 expression inhibitor binds to a region of SEQ. ID NO. 2. Optionally, the SIRT6 expression inhibitor binds to nucleotides 479-486, nucleotides 386-394, nucleotides 199-206, nucleotides 350-359 or nucleotides 455-463 of SEQ. ID NO. 2. Optionally, the SIRT6 expression inhibitor comprises micro-RNA. Optionally, the SIRT6 expression inhibitor comprises one or more of SEQ. ID NO. 3, SEQ. ID NO. 4, SEQ. ID NO. 5 and SEQ. ID NO. 6. Optionally, the agent comprises one or a combination of one or more of SEQ. ID NO. 7, SEQ. ID NO. 8, SEQ. ID NO. 9 and SEQ. ID NO. 10. Optionally, the agent is in the form of a composition in combination with a pharmaceutically acceptable carrier. Optionally, the composition is administered parenterally or optionally intravenously. Optionally, the subject is aged above 50 years old, above 65 years old or above 80 years old. Optionally, the daily dosage of agent administered is between 0.01 and 3000 mg daily.

There is further provided, in accordance with an embodiment of the invention, a method for treating cancer comprising administering to a human patient in need thereof an agent which decreases SIRT6 activity in cancer cells. Optionally, the agent decreases expression of the SIRT6 gene. Optionally, the agent comprises a SIRT6 expression inhibitor which binds to a 3'UTR region of human mRNA encoding SIRT6. Optionally, the SIRT6 expression inhibitor binds to a region of SEQ. ID NO. 2. Optionally, the agent binds to nucleotides 479-486, nucleotides 386-394, nucleotides 199-206, nucleotides 350-359 or nucleotides 455-463 of SEQ. ID NO. 2. Optionally, the SIRT6 expression inhibitor comprises miRNA. Optionally, the SIRT6 expression inhibitor comprises one or more of SEQ. ID NO. 3, SEQ. ID NO. 4, SEQ. ID NO. 5 and SEQ. ID NO. 6. Optionally, the agent is in the form of a composition in combination with a pharmaceutically acceptable carrier. Optionally, the composition is administered parenterally or intraveneously. Optionally, the daily dosage of agent administered is between 0.01 and 3000 mg daily.

In the description and claims of the present application, each of the verbs, "comprise," "include" and "have," and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

WORKS CITED

Kim D H, Rossi J J: Strategies for silencing human disease using RNA interference. Nat. Rev. Genet. 8, 173-184 (2007).

Wang, C., Li, Q., Redden, D. T., Weindruch, R. & Allison, D. B. Statistical methods for testing effects on 'maximum lifespan'. Mech. Ageing Dev. 125, 629-632 (2004).

Yuan et al. Aging in inbred strains of mice: study design and interim report on median lifespans and circulating IGF1 levels. *Aging Cell.* 2009.

The invention claimed is:

1. A method for treating an age-related disease comprising administering to a human subject above the age of 50 in need thereof an effective amount of an agent which increases the activity of sirtuin-6 (SIRT6) by increasing the expression of the SIRT6 gene, wherein the agent inhibits binding of a SIRT6 expression inhibitor to a 3'UTR region of human mRNA encoding SIRT6, wherein the expression inhibitor binds to nucleotides 479-486, of SEQ. ID NO. 2, and wherein the age-related disease is selected from the group consisting of: neurodegenerative disease, cancer, type 2 diabetes, hypertension, ocular disorders, cataracts, glaucoma, osteoporosis, blood clotting disorders, arthritis, hearing loss, stroke and Alzheimer's disease.

2. The method according to claim 1 wherein the SIRT6 expression inhibitor comprises micro-RNA.

3. The method according to claim 2 wherein the SIRT6 expression inhibitor comprises one or more of SEQ. ID NO. 3, SEQ. ID NO. 4.

4. The method according to claim 1 wherein the agent comprises one or a combination of one or more of SEQ. ID NO. 7, SEQ. ID NO. 8.

5. The method according to claim 1 wherein the agent is in the form of a composition in combination with a pharmaceutically acceptable carrier.

6. The method according to claim 5 wherein the composition is administered parenterally.

7. The method according to claim 5 wherein the composition is administered intravenously.

8. The method according to claim 1 wherein the subject is aged above 65 years old.

9. The method according to claim 1 wherein the subject is aged above 80 years old.

10. The method according to claim 1 wherein the daily dosage of agent administered is between 0.01 and 3000 mg daily.

11. The method according to claim 1 wherein the age-related disease is selected from the group consisting of ocular disorders, cataracts and glaucoma.

12. A method for treating an age-related disease comprising administering to a human subject above the age of 50 in need thereof an effective amount of an agent which increases the activity of sirtuin-6 (SIRT6) by increasing the expression of the SIRT6 gene, wherein the agent inhibits binding of a SIRT6 expression inhibitor to a 3'UTR region of human mRNA encoding SIRT6, wherein the expression inhibitor binds to nucleotides 386-394, nucleotides 199-206, nucleotides 350-359 or nucleotides 455-463 of SEQ. ID NO. 2, and wherein the age-related disease is selected from the group consisting of: neurodegenerative disease, cancer, type 2 diabetes, hypertension, ocular disorders, cataracts, glaucoma, osteoporosis, blood clotting disorders, arthritis, hearing loss, stroke and Alzheimer's disease.

13. The method according to claim 12 wherein the SIRT6 expression inhibitor comprises micro-RNA.

14. The method according to claim 13 wherein the SIRT6 expression inhibitor comprises one or more of SEQ. ID NO. 5 and SEQ. ID NO. 6.

15. The method according to claim 12 wherein the agent comprises one or a combination of one or more of SEQ. ID NO. 9 and SEQ. ID NO. 10.

16. The method according to claim 12 wherein the agent is in the form of a composition in combination with a pharmaceutically acceptable carrier.

17. The method according to claim 16 wherein the composition is administered parenterally.

18. The method according to claim 16 wherein the composition is administered intravenously.

19. The method according to claim 12 wherein the subject is aged above 65 years old.

20. The method according to claim 12 wherein the subject is aged above 80 years old.

21. The method according to claim 12 wherein the daily dosage of agent administered is between 0.01 and 3000 mg daily.

22. The method according to claim 12 wherein the age-related disease is selected from the group consisting of ocular disorders, cataracts and glaucoma.

* * * * *